(12) United States Patent
Smith et al.

(10) Patent No.: US 11,045,187 B2
(45) Date of Patent: Jun. 29, 2021

(54) SUBCUTANEOUS WOUND CLOSURE ASSEMBLY AND METHOD OF USE

(71) Applicant: BandGrip, Inc., Chicago, IL (US)

(72) Inventors: Fred Smith, Houston, TX (US); Keith Hoglund, Burr Ridge, IL (US); Tom Pruter, Lincolnshire, IL (US); Michael Lambert, Burr Ridge, IL (US)

(73) Assignee: BandGrip, Inc., Chicago, IL (US)

( * ) Notice: Subject to any disclaimer, the term of this patent is extended or adjusted under 35 U.S.C. 154(b) by 176 days.

(21) Appl. No.: 16/286,933

(22) Filed: Feb. 27, 2019

(65) Prior Publication Data
US 2019/0261980 A1    Aug. 29, 2019

Related U.S. Application Data

(60) Provisional application No. 62/636,221, filed on Feb. 28, 2018.

(51) Int. Cl.
*A61B 17/064* (2006.01)
*A61B 17/00* (2006.01)
*A61B 17/04* (2006.01)

(52) U.S. Cl.
CPC ...... *A61B 17/0644* (2013.01); *A61B 17/0057* (2013.01); *A61B 17/0401* (2013.01); *A61B 2017/00659* (2013.01); *A61B 2017/0427* (2013.01); *A61B 2017/0647* (2013.01)

(58) Field of Classification Search
CPC ............ A61B 17/0644; A61B 17/0057; A61B 17/0401; A61B 2017/0427; A61B 2017/00659; A61B 2017/0647
See application file for complete search history.

(56) References Cited

U.S. PATENT DOCUMENTS

| 4,430,998 | A | | 2/1984 | Harvey et al. | |
|---|---|---|---|---|---|
| 4,865,026 | A | * | 9/1989 | Barrett | A61F 13/00 606/214 |
| 5,603,145 | A | | 2/1997 | Arakawa et al. | |
| 5,968,097 | A | | 10/1999 | Frechet | |
| 6,485,503 | B2 | * | 11/2002 | Jacobs | A61B 17/064 606/151 |
| 6,652,559 | B1 | | 11/2003 | Tetreault | |
| 6,712,830 | B2 | | 3/2004 | Esplin | |
| 7,156,862 | B2 | | 1/2007 | Jacobs et al. | |
| 7,998,152 | B2 | * | 8/2011 | Frank | A61F 2/0063 606/151 |
| 8,029,532 | B2 | * | 10/2011 | Sirota | A61B 17/0057 606/213 |
| 8,500,759 | B2 | * | 8/2013 | Koyfman | A61F 2/0063 606/151 |

(Continued)

FOREIGN PATENT DOCUMENTS

WO    2016155891 A1    10/2016

*Primary Examiner* — Julian W Woo
(74) *Attorney, Agent, or Firm* — The Watson IP Group, PLC; Jovan N. Jovanovic

(57) ABSTRACT

A subcutaneous wound closure assembly having a closure apparatus, an insertion assembly and a retracting structure. The closure apparatus includes a substrate having a central axis and an outer perimeter. Radial ribs having micro needles extend therefrom. The insertion assembly includes an outer sheath and an applicator. Retracting structures in the form of sting members are coupled to the closure apparatus. A method of use is likewise set forth.

8 Claims, 14 Drawing Sheets

(56) References Cited

U.S. PATENT DOCUMENTS

| | | | |
|---|---|---|---|
| 8,617,206 B2 | 12/2013 | Sargeant et al. | |
| 8,894,683 B2* | 11/2014 | Weadock | A61B 17/0401 |
| | | | 606/215 |
| 8,945,156 B2 | 2/2015 | Kubiak et al. | |
| 8,961,594 B2* | 2/2015 | Maisano | A61B 17/00234 |
| | | | 623/2.17 |
| 9,492,261 B2* | 11/2016 | Cohen | A61F 2/0063 |
| 2004/0087980 A1 | 5/2004 | Ford et al. | |
| 2005/0256532 A1* | 11/2005 | Nayak | A61B 17/0057 |
| | | | 606/151 |
| 2006/0106420 A1* | 5/2006 | Dolan | A61B 17/0057 |
| | | | 606/213 |
| 2008/0147099 A1 | 6/2008 | Uen | |
| 2009/0254103 A1* | 10/2009 | Deutsch | A61F 2/0063 |
| | | | 606/151 |
| 2011/0106247 A1* | 5/2011 | Miller | A61B 17/0401 |
| | | | 623/2.17 |
| 2015/0305739 A1 | 10/2015 | Rolandi et al. | |
| 2017/0333039 A1 | 3/2017 | Leung | |

\* cited by examiner

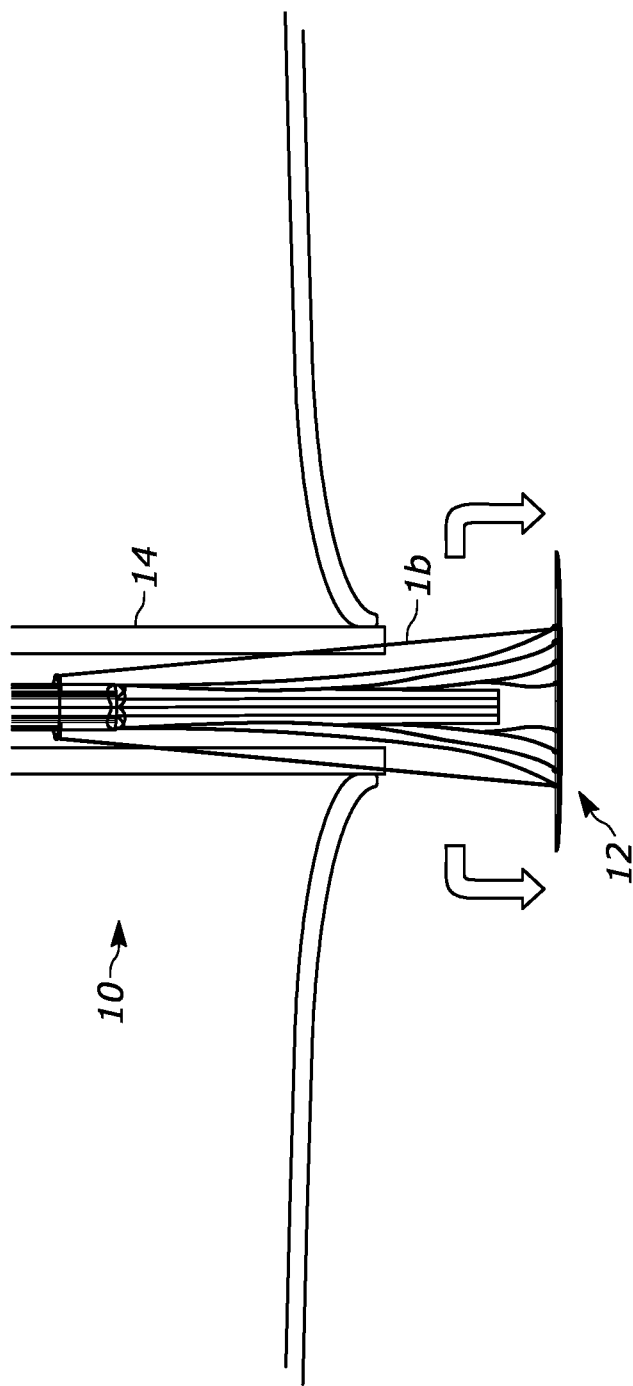

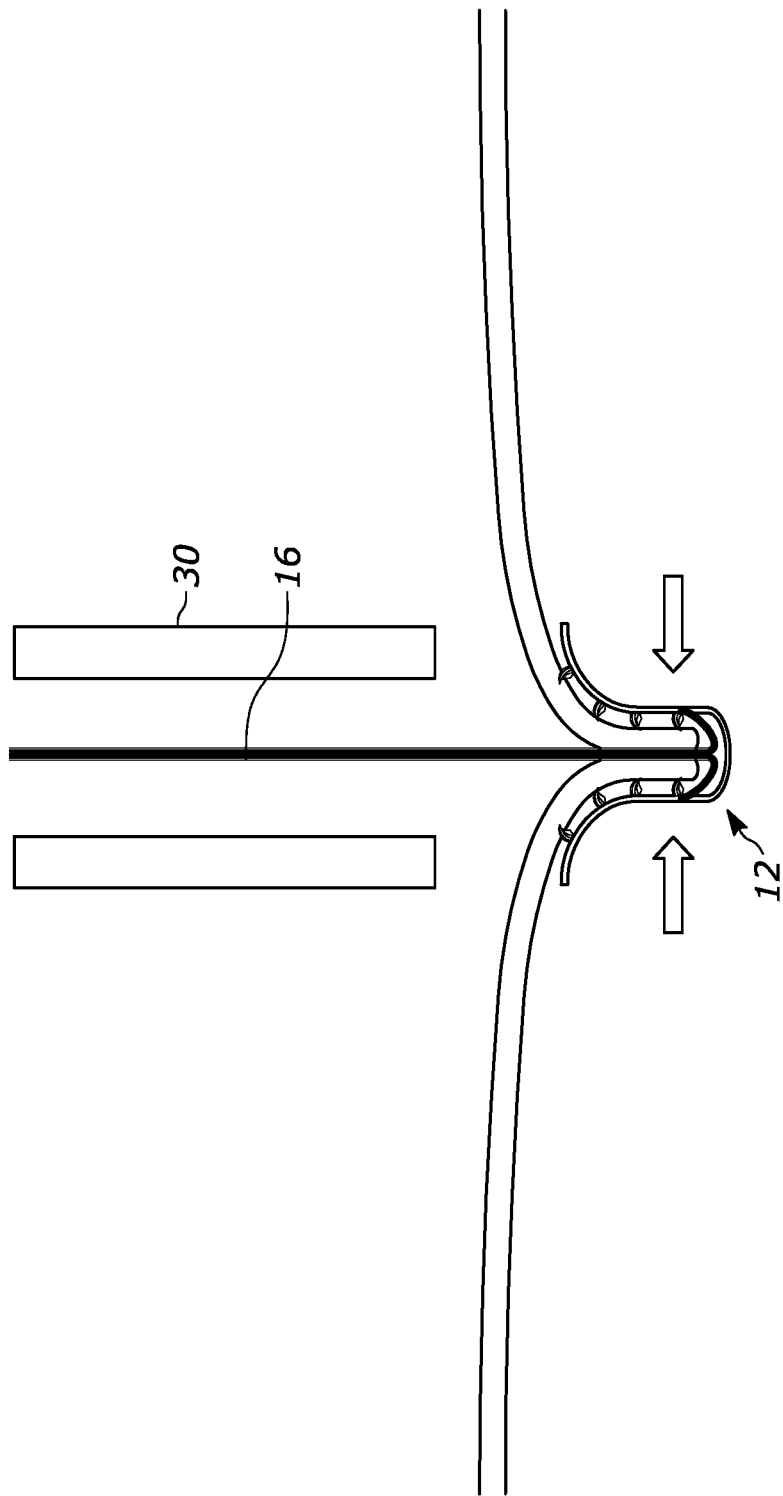

SUBCUTANEOUS WOUND CLOSURE ASSEMBLY AND METHOD OF USE

CROSS-REFERENCE TO RELATED APPLICATION

The present application claims priority from U.S. Pat. App. Ser. No. 62/636,221 filed Feb. 28, 2018, entitled Subcutaneous Wound Closure Assembly and Method of Use, the entire specification of which is hereby incorporated by reference in its entirety.

The present application is related to, but does not claim priority from, International Patent Application Serial No. PCT/US2016/061584 filed Nov. 11, 2016, entitled Bandage, which is attached hereto in Appendix A, as well as to U.S. patent application Ser. No. 15/801,529, filed Nov. 2, 2017, entitled Bandage and Anchor for a bandage. The entire specification of both of these applications is hereby incorporated by reference in its entirety.

BACKGROUND OF THE DISCLOSURE

1. Field of the Disclosure

The disclosure relates in general to wound closures, and more particularly, to a subcutaneous wound closure assembly as well as a method of using a subcutaneous wound closure assembly for the closure of a wound opening, which, in some configurations, extends into the body cavity of a patient.

2. Background Art

The use of wound closure structures and the like are well known in the art. In certain instances, a wound opening is of the type that extends into a body cavity of a patient. The wound opening may be the result of an accident or injury, or the result of surgery or treatments.

Typically, to close such a wound, the wound opening is brought together and typically, a suture is utilized to close the wound. In other configurations, other suture replacements may be utilized. In some instances, suturing below the epidermis may be utilized in association with other sutures or bandages or buttresses on the outside of the body (across the epidermis).

In many instances, the result of such wound closure methods is that scarring can result. In other instances, the suturing may be painful. In still other instances, the wound may reopen.

SUMMARY OF THE DISCLOSURE

The disclosure is directed a closure apparatus for use in a subcutaneous wound closure assembly. The assembly comprises a substrate having an inner surface and an outer surface, a central axis and an outer perimeter. The substrate has a plurality of ribs extending radially outward from the central axis. The radial ribs have a plurality of micro needles extending therefrom.

In another aspect of the disclosure, the disclosure is directed to a subcutaneous wound closure assembly comprising a closure apparatus, an insertion apparatus and a retracting structure coupled to the closure apparatus.

In some configurations, the subcutaneous wound closure assembly is configured so that the insertion apparatus further comprises an outer sheath and an applicator, with the applicator being slidably insertable within the outer sheath.

In some configurations, the retracting structure comprises a plurality of string members coupled to the closure apparatus and extending through the outer sheath.

In another aspect of the disclosure, the disclosure is directed to a method of using a subcutaneous comprising the steps of: positioning an outer sheath proximate a wound opening with a distal end opening being position proximate thereto; folding a closure apparatus into a folded configuration; directing the closure apparatus through the outer sheath beyond the wound opening with an applicator; unfolding the closure apparatus beyond the wound opening; engaging tissue surrounding the wound opening with micro needles; pulling the closure apparatus with a retracting structure; and directing the closure structure into a clinching configuration with the retracting structure, to, in turn, close the wound opening.

In some configurations, the wound opening is closed without the need for a suture applied about the wound opening.

BRIEF DESCRIPTION OF THE DRAWINGS

The disclosure will now be described with reference to the drawings wherein:

FIGS. 5a and 5b of the drawings are partial cross-sectional views of a subcutaneous wound closure assembly in operation, showing, the insertion of the closure assembly, and the deploying of the same from the folded orientation to the deployed orientation;

FIGS. 7a and 7b of the drawings are partial cross-sectional views of a subcutaneous wound closure assembly in operation, showing, the clinching configuration of the closure substrate, the further pulling of the retracting structure, and the removal of the outer sheath of the insertion assembly;

DETAILED DESCRIPTION OF THE DISCLOSURE

Figure 2:
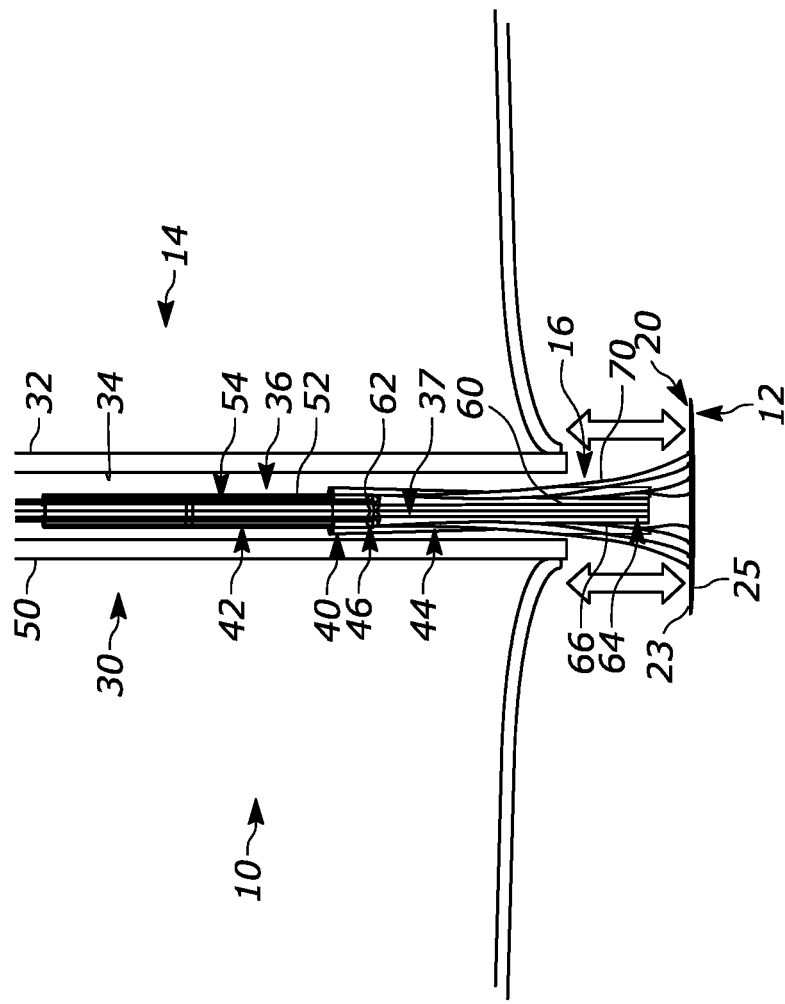
FIG. 2 of the drawings is a cross-sectional view of the subcutaneous wound closure assembly in operation, showing, in particular, a procedure utilizing the same.

While this disclosure is susceptible of embodiment in many different forms, there is shown in the drawings and described herein in detail a specific embodiment(s) with the understanding that the present disclosure is to be considered as an exemplification and is not intended to be limited to the embodiment(s) illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
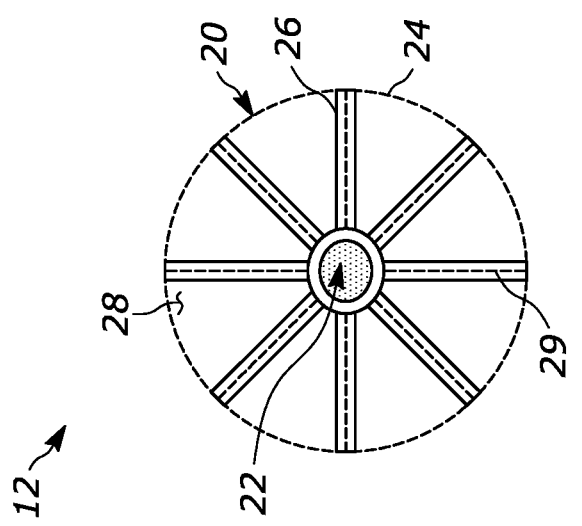
FIG. 1 of the drawings is a bottom plan view of a configuration of the closure assembly configured for use in association with the subcutaneous wound closure assembly.
Figure 3:
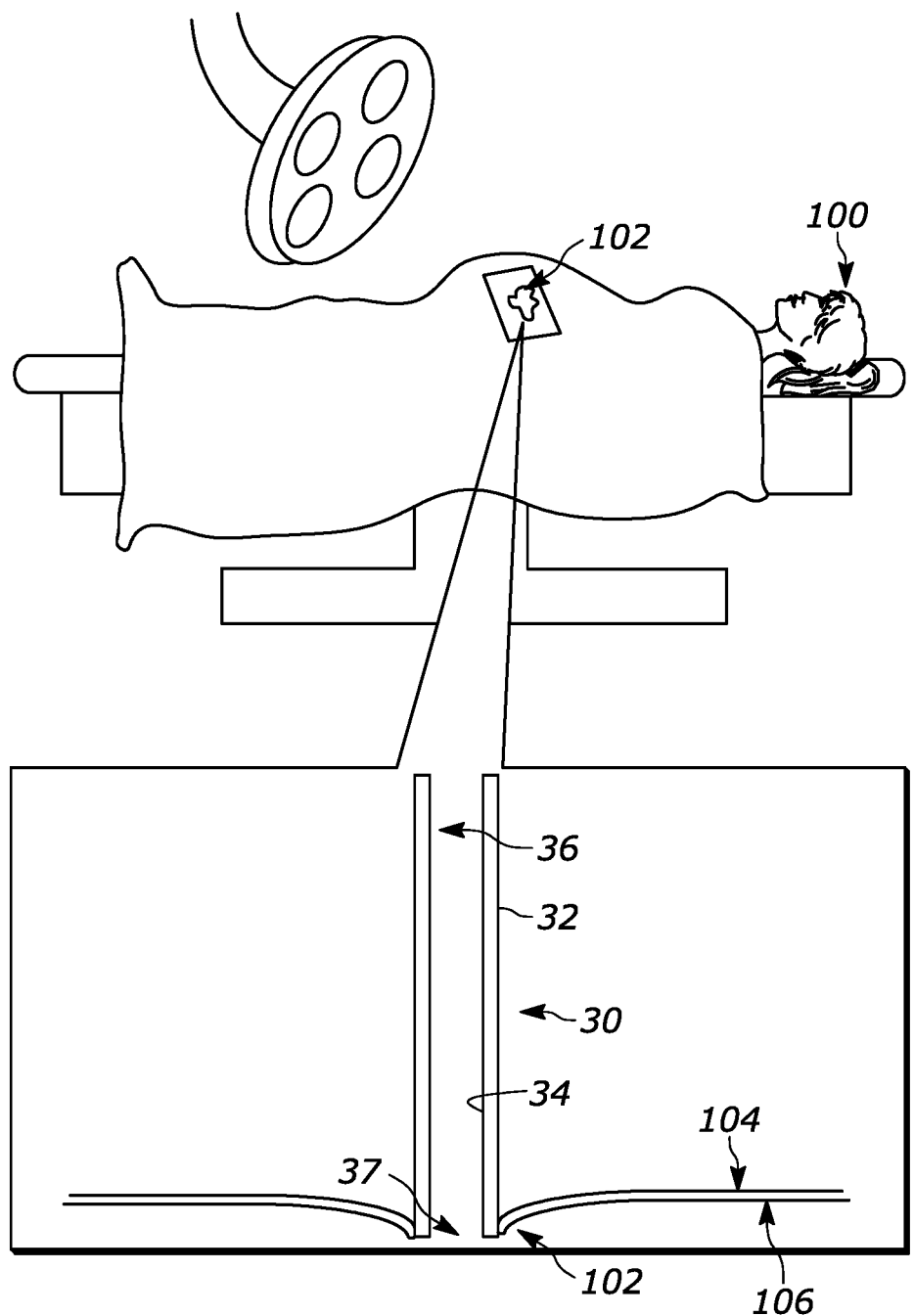
FIG. 3 of the drawings is a side elevational view with a partial magnification of a patient having a wound and an outer sheath positioned in an operable position so as to initiate a procedure utilizing the subcutaneous wound closure assembly.

Referring now to the drawings and in particular to FIG. 1, the subcutaneous wound closure device is shown generally at 10. The subcutaneous wound closure assembly is configured for use in procedures to close a wound that extends through the tissue of a patient, and into the body cavity, for example (although it is not limited thereto). The subcutaneous wound closure assembly can be utilized for a number of different wounds of different sizes, and configurations. There is no particular limitation on the type of wound with which the assembly can be utilized.

The subcutaneous wound closure assembly 10, with reference to FIGS. 1 and 2, comprises closure apparatus 12, insertion assembly 14 and retracting structure 16. The closure apparatus is shown in greater detail in FIG. 1 as comprising substrate 20, which can be positioned between different orientations, including a folded (or undeployed) orientation, an unfolded (or deployed) orientation and a clinching orientation. The substrate 20 is defined by an inner surface 23 and an outer surface 25 and includes a central axis 22 with an outer perimeter 24. In the configuration shown, the outer perimeter comprises a generally circular configuration. It is, however, envisioned that a number of different shapes are contemplated, including, but not limited to square, arbitrary, elliptical, polygonal among others.

The substrate 20 includes, in the configuration shown, a plurality of radial ribs 26 that extend radially outwardly from a region at or near the central axis toward or to the outer perimeter. The inner surface of the radial ribs includes a plurality of micro structures 29 that extend from the base surface 142. Such micro structures may be of the type disclosed as gripping structures (70) in the above-incorporated, and attached, '584 PCT application, or the gripping structures (70) of the incorporated, and attached, '529 application. In the configuration shown, the micro structures (or gripping structures) are shown as comprising a plurality of such structures arranged in an outwardly radially linear fashion. In other configurations, multiple gripping structures having different arrangements are contemplated for use. In the configuration shown, the gripping structures are integrally formed with the radial ribs (which may all be formed together, or individually), with the gripping structures being pointed radially inward toward or to the central axis.

More specifically, and as explained in the incorporated applications, the microneedles (also termed gripping structures are disclosed with reference to FIGS. 8 through 15 are shown as comprising a base configuration 160 and upstanding structure 170. The base configuration further comprises a leading edge 162, first rearward trailing edge 164, second rearward trailing edge 166, and rear intersection region 168. In the configuration shown, the base configuration 160 substantially defines a triangle, with the leading edge being substantially perpendicular to a longitudinal axis of the leading edge. The first and second rearward trailing edges 166, 168 together with the leading edge 155 define an isosceles triangle with the rear intersection region 168 defining the third point of the triangle. It has been found that a triangular cross-sectional configuration with the leading edge being perpendicular to the direction of force (i.e., the biasing force of the bandage or other structure to direct the wound to closure) and inboard of the rear intersection region exhibits improved strength characteristics and retention characteristics that a configuration that wherein the base configuration is flipped.

In the configuration shown, the leading edge is nominally 0.017 inches in width. The depth of the base structure, that is from the rear intersection region 68 to the leading edge is nominally 0.0156 inches. As such, width is slightly greater than the depth, defining a generally isosceles triangle.

The upstanding structure further comprises a front curved wall 171, first trailing wall 172, second railing wall 173, first upstanding edge 174, second upstanding edge 175, outer backbone 176, tip 178, and overhanging portion 180.

The front curved wall 171 extends from the leading edge 162 of the base. Similarly, the first trailing wall 172 extends from the first rearward trailing edge 164 and the second trailing wall 173 extends from the second rearward trailing edge 166. From these walls, the edges are created. That is, the first upstanding edge 174 is defined by the intersection between the front curved wall 171 and the first trailing wall 172. The second upstanding edge 175 is defined by the intersection between the front curved wall 171 and the second trailing wall 173. The outer backbone 176 is defined as the intersection between the first trailing wall 172 and second trailing wall 173 and extends from the rear intersection region 68. The intersection of all the walls extending from the base configuration defines the tip 178. The tip 178, due to the arcuate configuration of the outer back bone, and the first and second upstanding edges, defines a tip axis 188, which is generally controlled by the outer backbone the tip 178. In the configuration shown the tip axis is within a few degrees of being parallel to the lower surface of the base 142, and, is preferably forms an angle α with a horizontal line intersecting at the tip of between −10° and 10°, and more preferably between −1° and 5°. It will be understood that in such a configuration, the axis is generally rather horizontal and facing in the direction of the force exerted by the inward biasing of the gripping structures.

In the configuration shown, the outer backbone is defined by multiple arcs, and in the configuration shown, three different arcuate configurations. The front curved wall is defined by multiple arcs, and in the configuration shown, two different arcuate configurations.

The overhanging portion 180 begins noticeably following the interface plane 182, or the plane perpendicular to the base 142 bisecting the upstanding structure 170 through the leading edge 162. Consequently, the base 183 of the interface plane 182 is collinear to the leading edge 162 of the base configuration 160. The intersection of these lines atop the upstanding structure 70 creates the top meeting region 86. In the configuration shown, the overall depth of the gripping structure, that is from the tip to the outer backbone at the base configuration is nominally 0.029 inches. The height of the tip from the base is nominally 0.0230 inches. When compared to the thickness of the base, which is nominally 0.005 inches, the height is 4.6 times the thickness of the base. Whereas the base has a thickness which is similar to the thickness (or slightly thicker or thinner) than the epidermis, the tip is intended to extend beyond the epidermis and into the dermis of the patient or user. As such, it is desirable that the height is preferably 2 times the thickness of the base, and more preferably 4 or more times the thickness of the base. It will be understood that in other configurations, the upstanding structure may be contained within the structure of the base configuration, and may not include an overhanging portion, while still including a tip as disclosed above that is directed toward the central region of the base substrate.

The overhang portion, that is the amount the tip is spaced apart from the leading edge is nominally 0.134 inches. Thus, the overhang portion extends beyond the footprint of the gripping structure (i.e., beyond the leading edge of the base configuration) by a distance that is approximately 85% of the depth of the gripping structure at the base configuration.

Attention should be given to the overhand portions 180 of each of the upstanding structures, as its complexity begets a difficulty in classic molding mechanisms when molded with the base 142. One skilled in the art may be familiar with the difficulty to mold materials with an overhand, or lip in the material, that can create a force to cement the molded object to the mold itself. The existence of these overhangs along the gripping structures, further added to the plurality of structures, creates a complex molding procedure. To mold the configuration shown, it is necessary to translate the mold in a direction that is perpendicular to the direction of removal of the member from the mold. That is, the molded member is first slid along the mold and then slid out of the mold. It may further be necessary to slightly rotate the molded member while being removed.

A web 28 extends radially from the central axis and between the radial ribs. The web 28 comprises, preferably a more flexible material that can fold over itself when in the folded or undeployed configuration. In other configurations, the radial ribs and the web may be integrally formed, or may be separately formed and coupled together. In other configurations, the structures may be co-molded. In still other configurations, the radial ribs and the web may be formed from the same material, wherein the microneedles can be co-molded, or likewise formed from the same material. In other configurations, the web 28 may be omitted, and the substrate is defined by a plurality of radially outward ribs, which may be coupled to the central axis, or near the central axis. In other configurations, the web may comprise frangible members.

Depending on the configuration, the substrate may comprise a material that includes polymers and/or metal members. In some configurations, the substrate is configured to dissolve within the body, after a predetermined time, which may comprise anytime between a few days to months, depending on composition and desired use.

With reference to FIG. 2, the insertion assembly is shown as comprising outer sheath 30 and applicator 40. The outer sheath 30, in the form of an elongated tube, includes outer surface 32 and inner surface 34. In the configuration shown, the elongated tube has a substantially uniform circular cross-section defining an elongated channel 36 which is substantially uniformly cylindrical, and defines a distal end opening 37. The outer sheath comprises a generally rigid material having a shape retaining ability, and which can withstand the application of forces during the execution of the procedure. In some configurations, the outer sheath may comprise a transparent structure which allows for the monitoring of the procedure and the operation of the applicator, the substrate and the retracting structure in use.

The applicator 40 is shown in FIG. 2 as comprising elongated handle 42, applicator fork 44 and string gathering openings 46. The applicator generally comprises a relatively rigid member that is capable of directing the closure apparatus through the outer sheath and into the deployed or unfolded configuration. The elongated handle 42 extends between a proximal end 50 and a distal end 54, and defines a channel opening 54 that extends from the proximal end to the distal end. The elongated handle is sized so as to be manipulatable by the user beyond the end of the outer sheath.

The applicator fork comprises a plurality of tines, such as tine 60, which extends outwardly from the distal end of the elongated handle. The tines are radially spaced apart from each other so as to define a plurality of slots therebetween. The tines may have some flexibility to have the distal end 64 thereof flex inwardly and outwardly, in a radial fashion and/or an axial fashion. The tines further include a proximal end 62 that meets the distal end 52 of the elongated handle 42. In the configuration shown, the different tines are spaced apart radially, and may be equidistantly spaced from each other so that the slots therebetween are substantially uniform. For example, two tines, spaced 180° apart may be utilized, or three tines, spaced 120° apart, or four tines, spaced 90° apart, among other configurations. In the configuration shown, the elongated handle and the applicator fork may be formed together as an integrated member (such as, through molding or the like).

The string gathering openings 46 may be disposed proximate the interface between the elongated handle and the applicator fork, or may be disposed on either one or both of the elongated handle or the applicator fork. In some configurations, the openings may be located along one location between the distal end of the applicator fork, and the proximal end of the elongated handle. In other configurations, multiple openings disposed along either one or both of the elongated handle and/or the applicator fork are contemplated. In some configurations, the number of string gathering openings may be varied depending on the size of the wound opening, and the size of the closure apparatus, for example.

The retracting structure 16 comprises a plurality of string members 70, each having a grasping end 72 and closure end 74. The grasping end 72 extends beyond the outer sheath so as to be graspable by a user by hand or with a tool (such as forceps, not shown, or the like). The closure end 74 is attached to the substrate 20. In the configuration shown, the string members 70 are coupled to the substrate radially outwardly from the central axis, and between the central axis and the outer perimeter. In some configurations, the string members are tied to openings, or structures on the closure apparatus, in, for example, the form of knots or the like. In other configurations, the string members 70 may have their closure ends 74 integrally molded into the substrate (for example, into the radial ribs or the like).

The string members 70 may comprise suture, for example, as well as polymers, natural fibers, as well as metal wire. In some configurations, the string members are configured to dissolve within the patient. In other configurations, the string members may remain within the body. In still other configurations, combinations of the foregoing are contemplated. In still other configurations, the string members may be utilized in a suture process after installation of the closure apparatus.

The operation of the device will be described in conjunction with reference to FIGS. 3 through 7. In particular, and with reference to FIG. 3, a patient 100 has received a wound, defining a wound opening 102. The wound has generally penetrated into the body cavity, thereby defining inner tissue surface 106 and outer tissue surface 104. To initiate the procedure, the outer sheath 30 is positioned to overlie (or partially extend into) the wound opening 102. Once positioned, a closure apparatus 12 is prepared with retracting structure 16 attached to closure apparatus 12.

In particular, the retracting structures are coupled to the closure apparatus and then extended into or otherwise attached to the applicator. Once attached, the closure apparatus is directed into the folded, or undeployed configuration (much like a folded umbrella), about the distal end of the applicator fork. The string members are extended out the distal end of the elongated handle and the outer sheath.

Figure 4A:
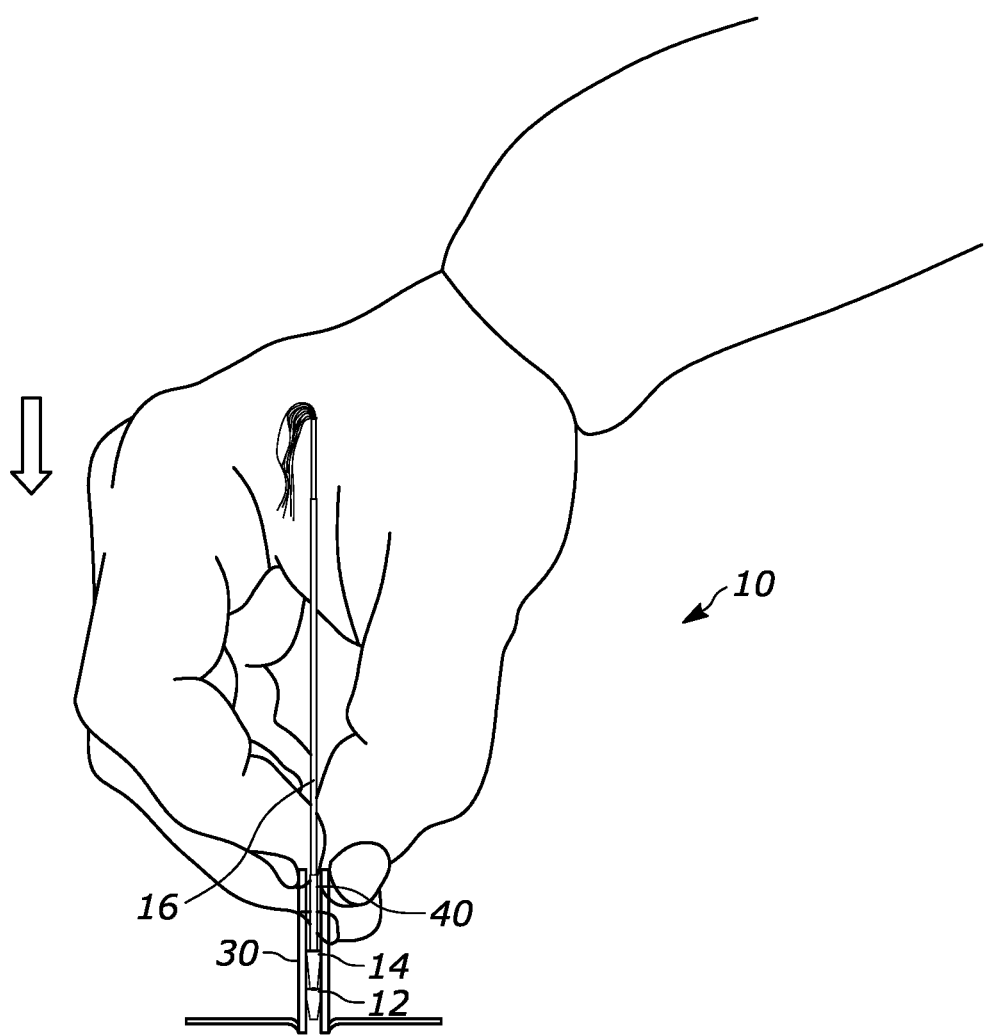
FIGS. 4a and 4b of the drawings are a partial cross-sectional views of a subcutaneous wound closure assembly in operation, showing, initially, the closure assembly in a folded, or undeployed, orientation within the insertion assembly, as the procedure is initiated.
Figure 4B:
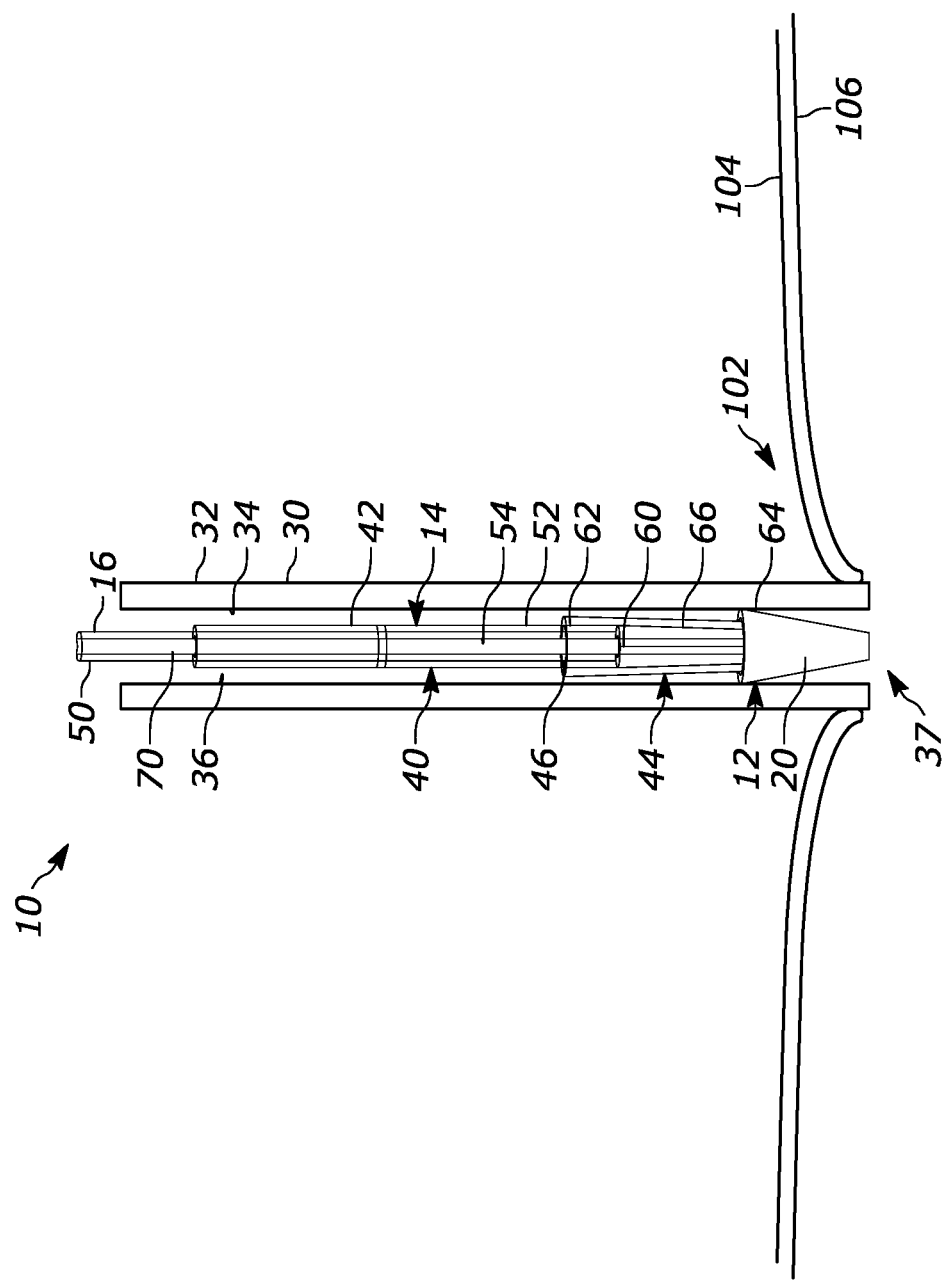

Once prepared, and with reference to FIGS. 4a and 4b, the applicator together with the closure apparatus and the retracting structure are extended into the outer sheath. The outer sheath assists with maintaining the closure apparatus in the folded configuration. It is contemplated that the outer perimeter of the substrate of the closure apparatus slidably moves along the inner surface of the outer sheath in an abutting configuration. The applicator fork precludes further inward movement and folding of the closure apparatus.

Figure 5A:
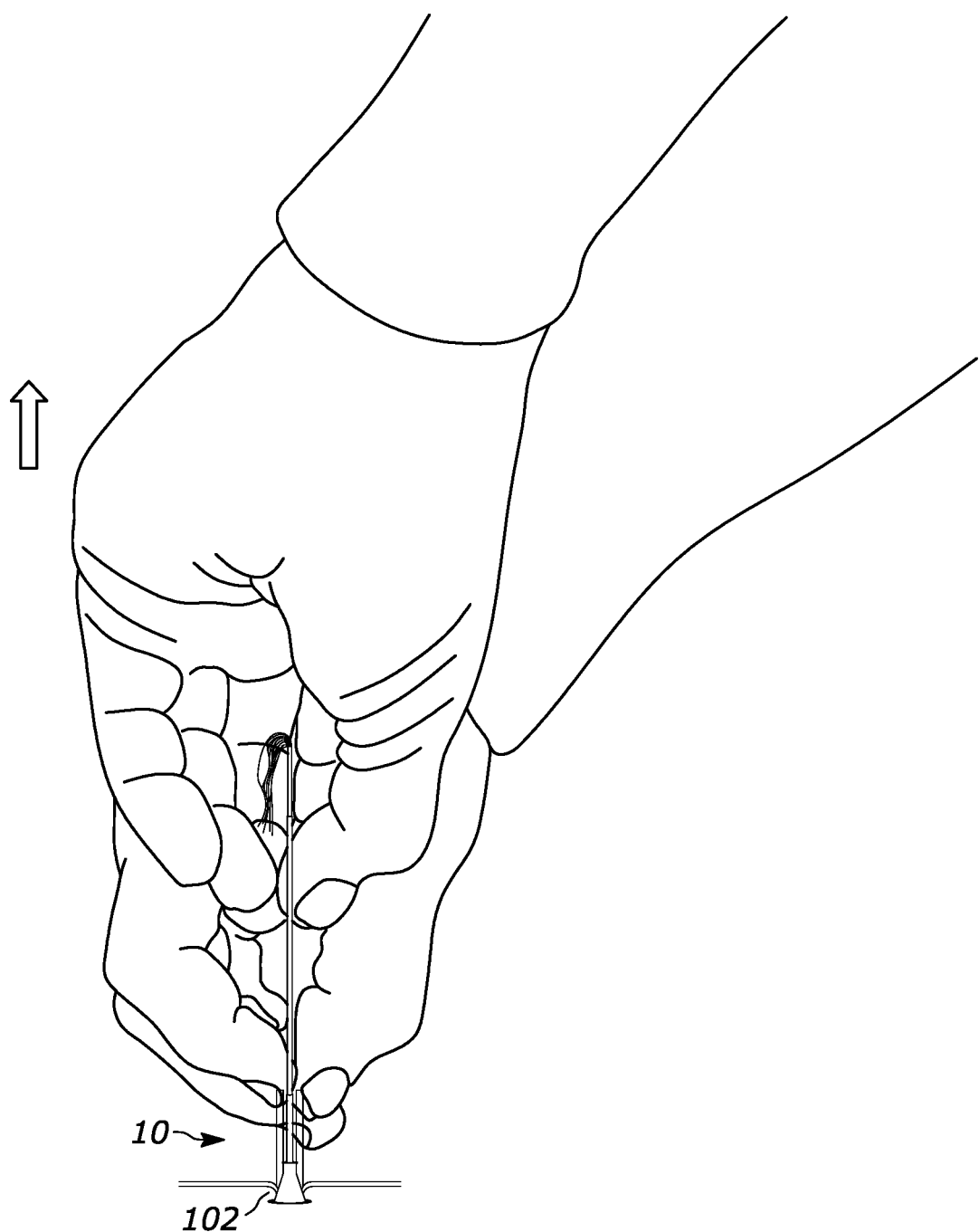

Continued insertion eventually directs the closure apparatus and the applicator beyond the distal end opening of the outer sheath. With reference to FIGS. 5a and 5b, once extended beyond the outer sheath, the closure apparatus springs outwardly into the unfolded or deployed configuration. In some configurations, the outward movement is caused by the natural resilience of the material (wherein, when folded, the closure apparatus is biased in an outward direction). In other configurations, gravity or the string members may further aid in the positioning of the closure apparatus into the unfolded or deployed configuration as the closure member extends out of the outer sheath.

Figure 6A:
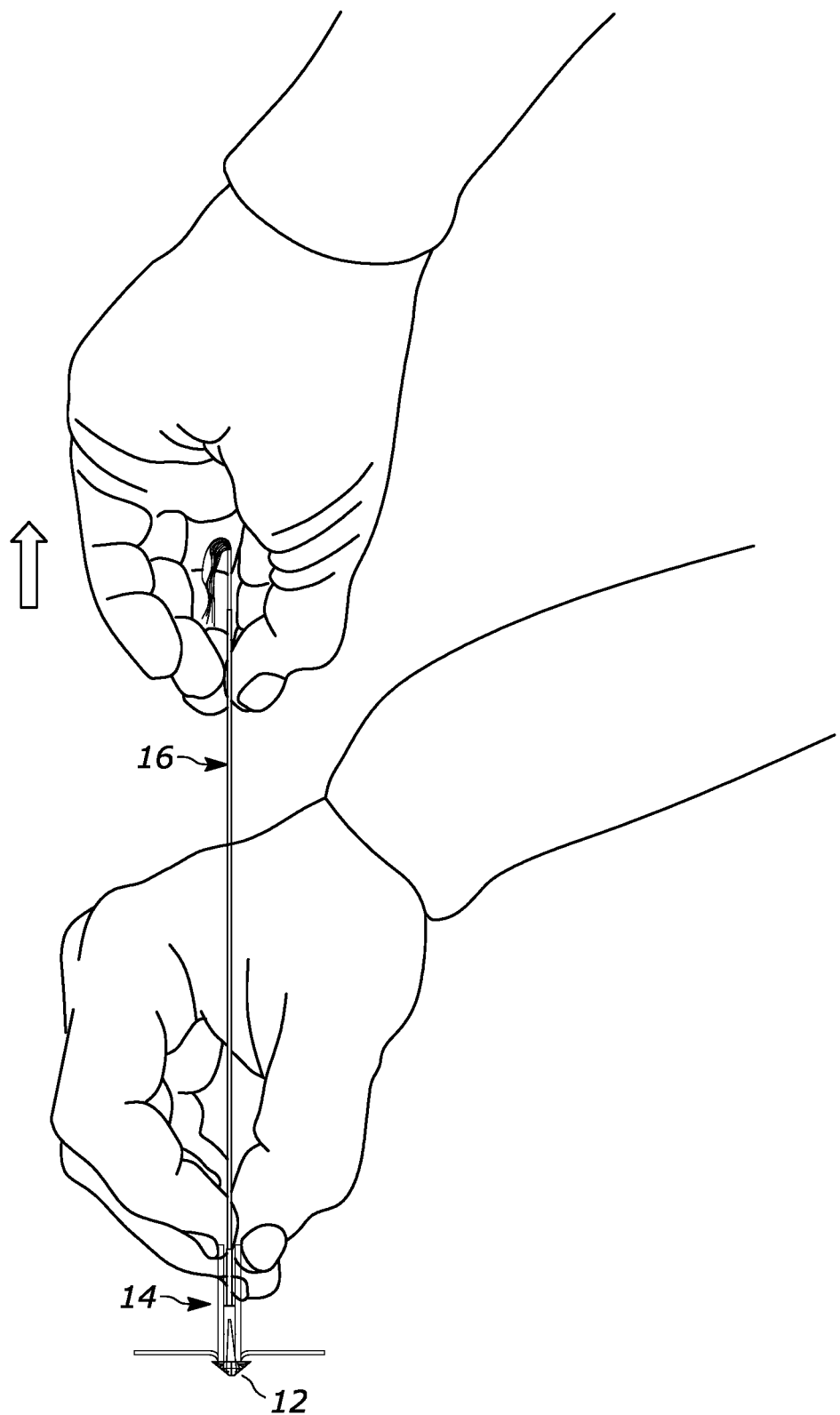
FIGS. 6a and 6b of the drawings are partial cross-sectional views of a subcutaneous wound closure assembly in operation, showing, the manipulation of the retracting structures, while retaining the outer sheath, to initiate the mechanical coupling of the closure assembly with the inner surface of the patient, so as to pinch the tissue around the wound opening, and to be directed into a clinching configuration.
Figure 6B:
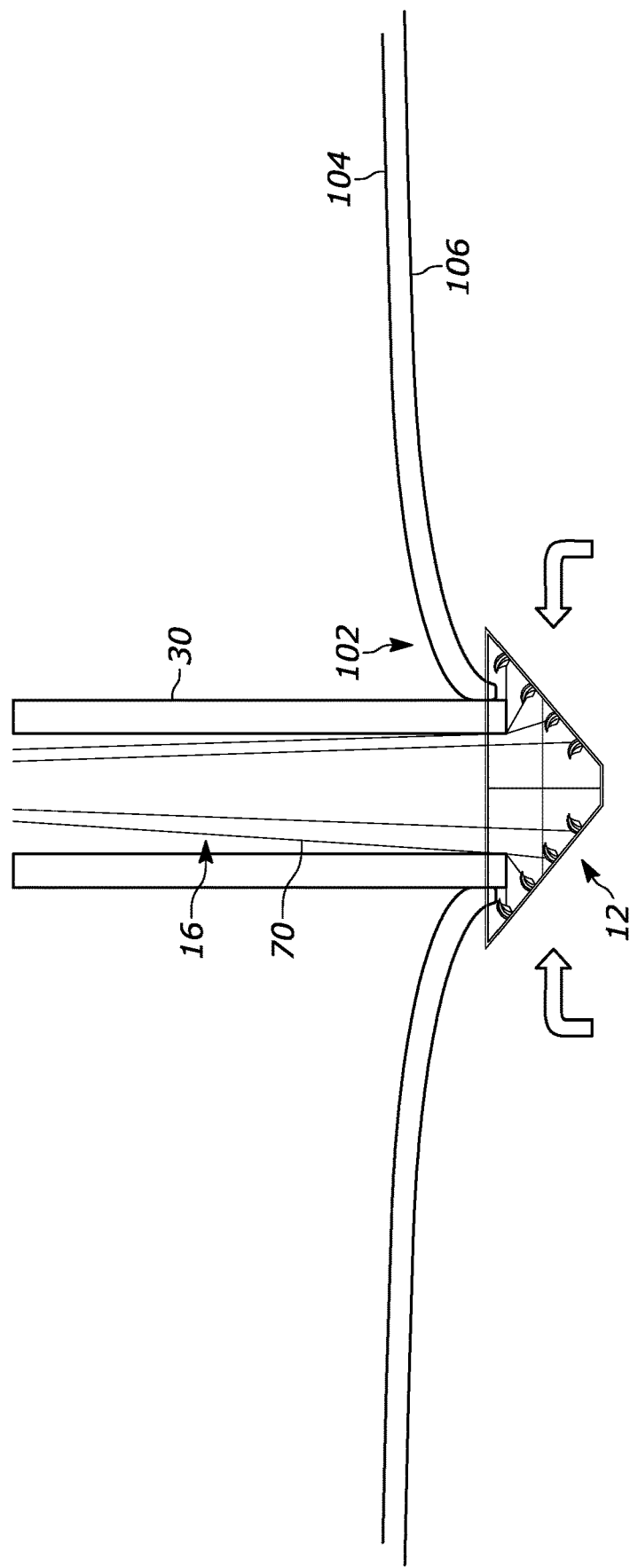
Figure 7A:
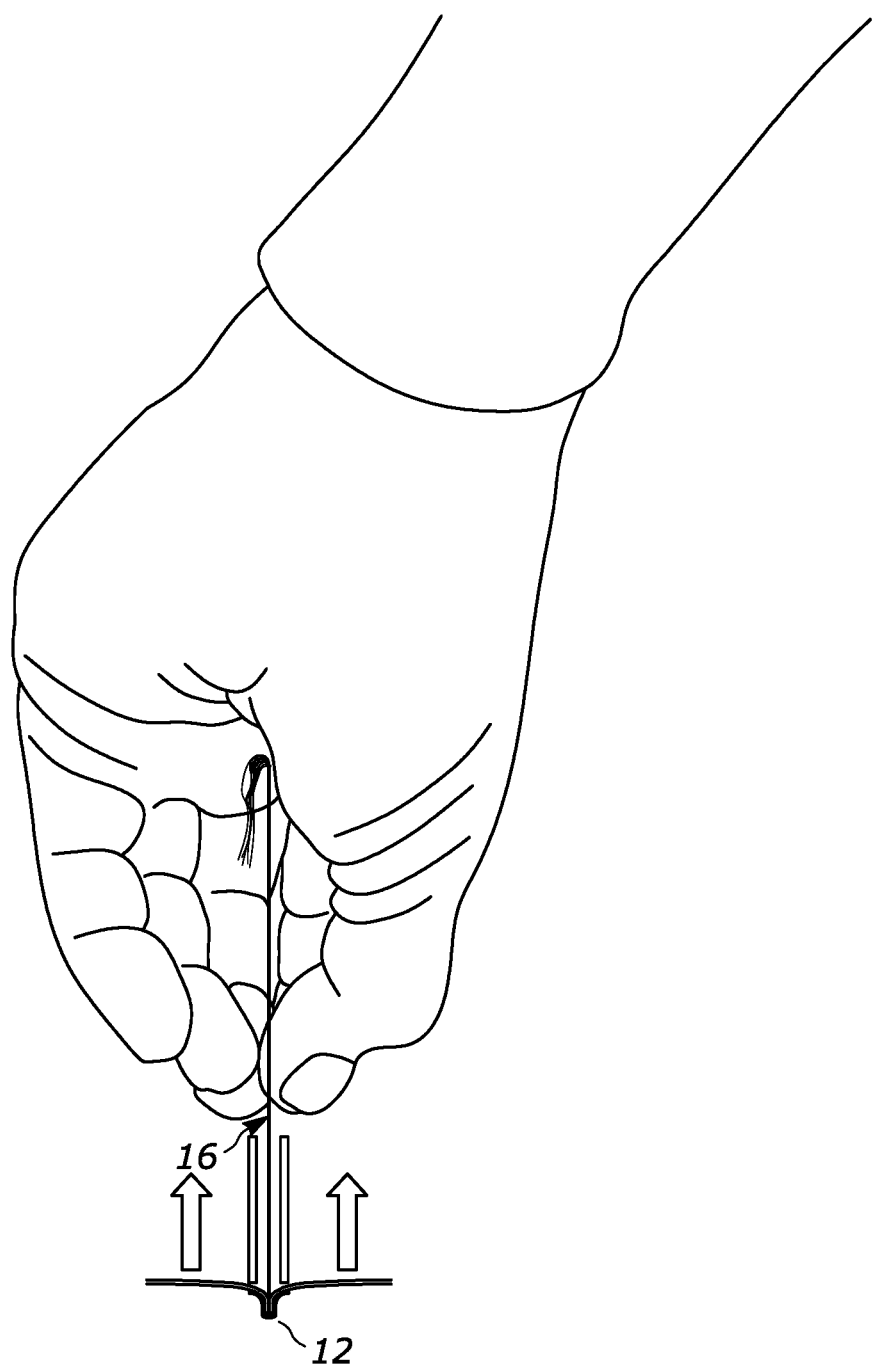
Figure 8:
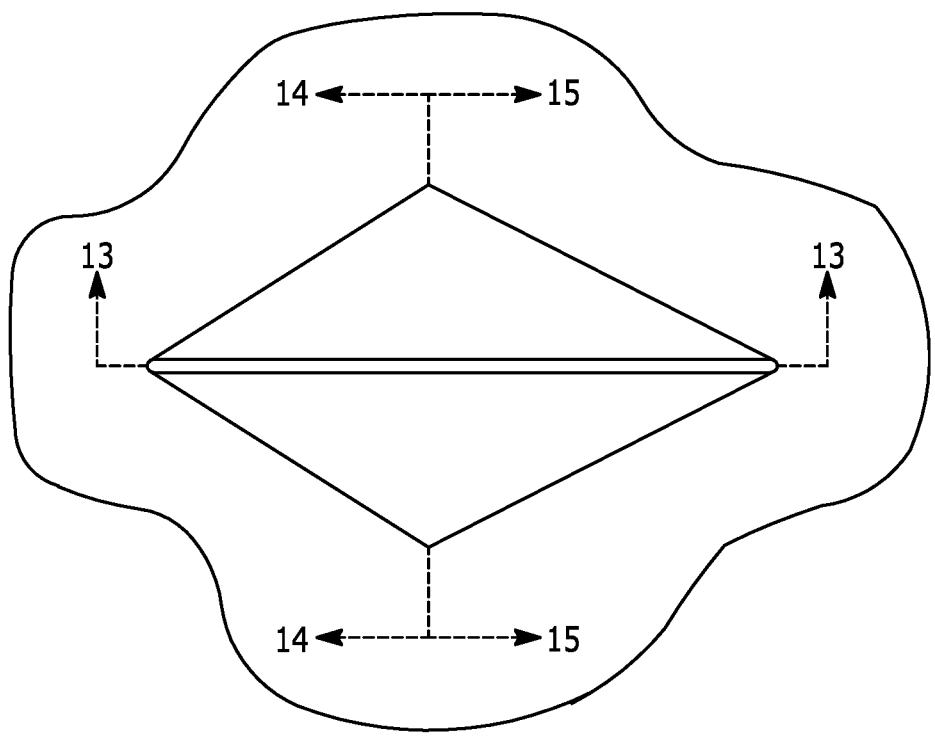
FIG. 8 of the drawings is a top plane view of the mechanical coupling system showing, in particular, an upstanding structure.
Figure 9:
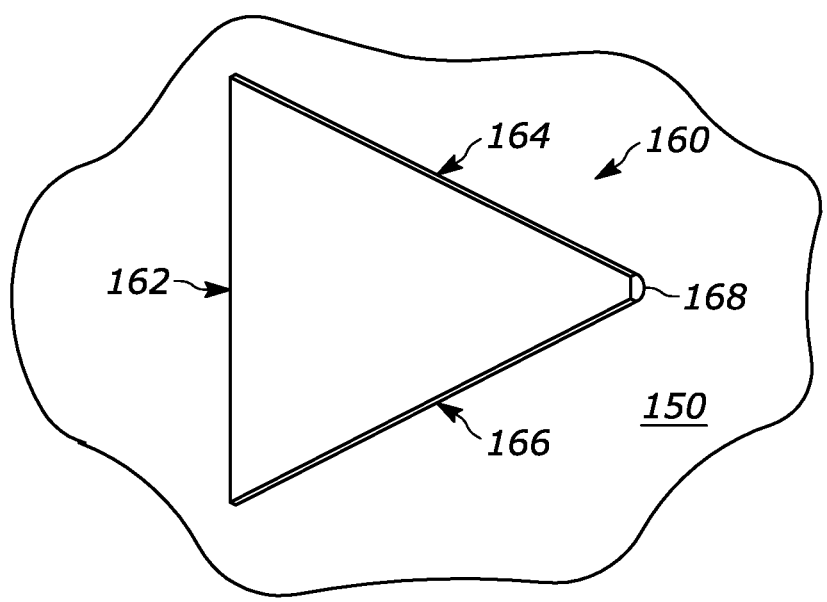
FIG. 9 of the drawings is a cross sectional view of the gripping structure, taken generally about a line parallel to the base of the radial ribs, showing, in particular, the base configuration thereof.
Figure 10:
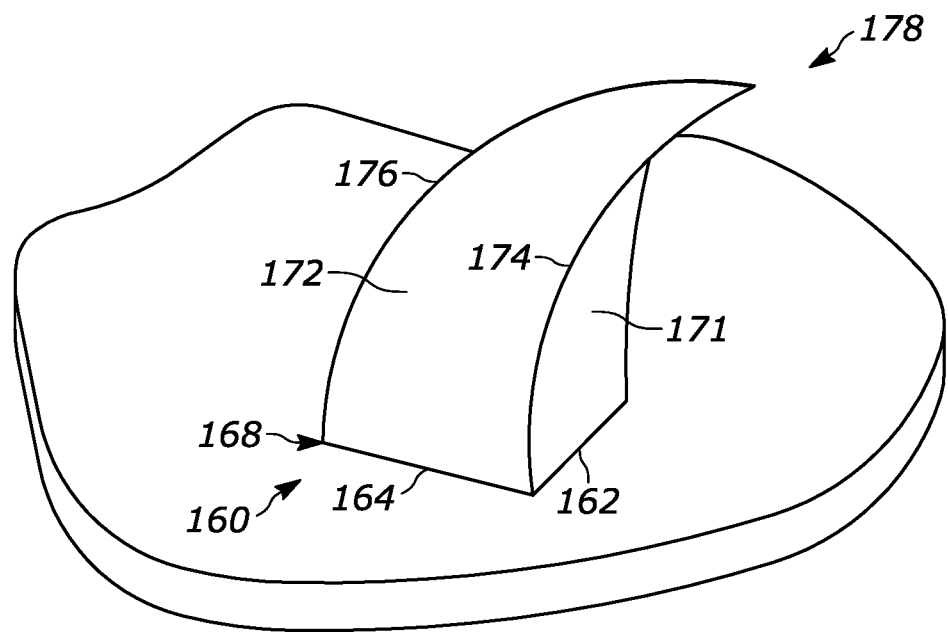
FIG. 10 of the drawings is a partial perspective view of the gripping structure showing, in particular, the upstanding structure.
Figure 11:
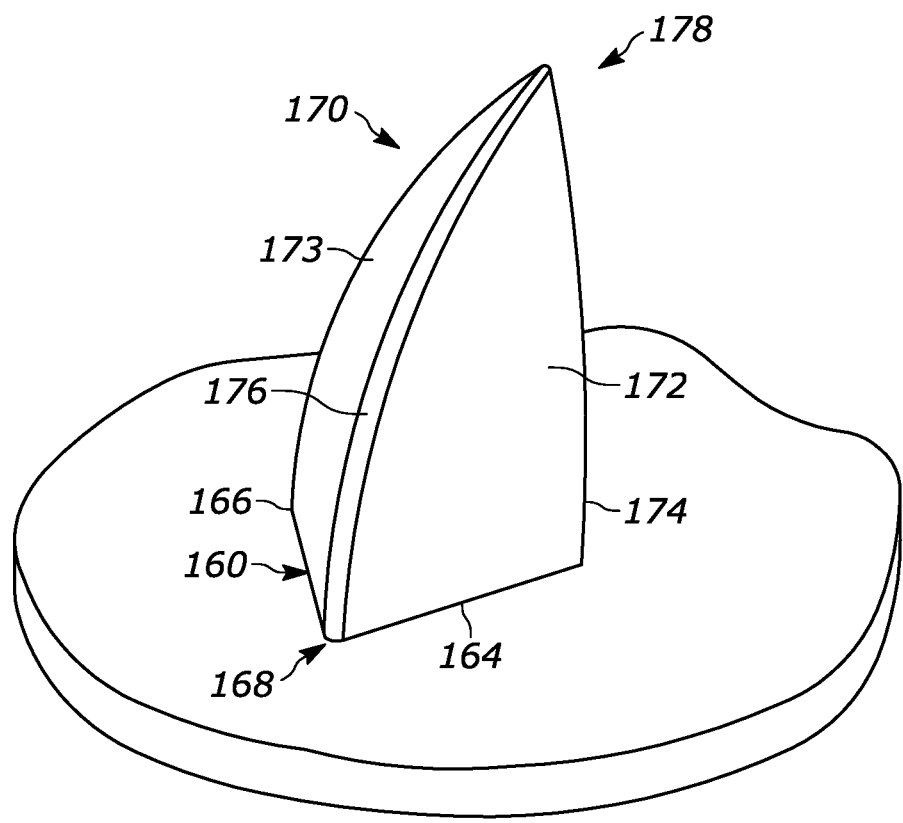
FIG. 11 of the drawings is a perspective view of the gripping structure showing, in particular, an upstanding structure.
Figure 12:
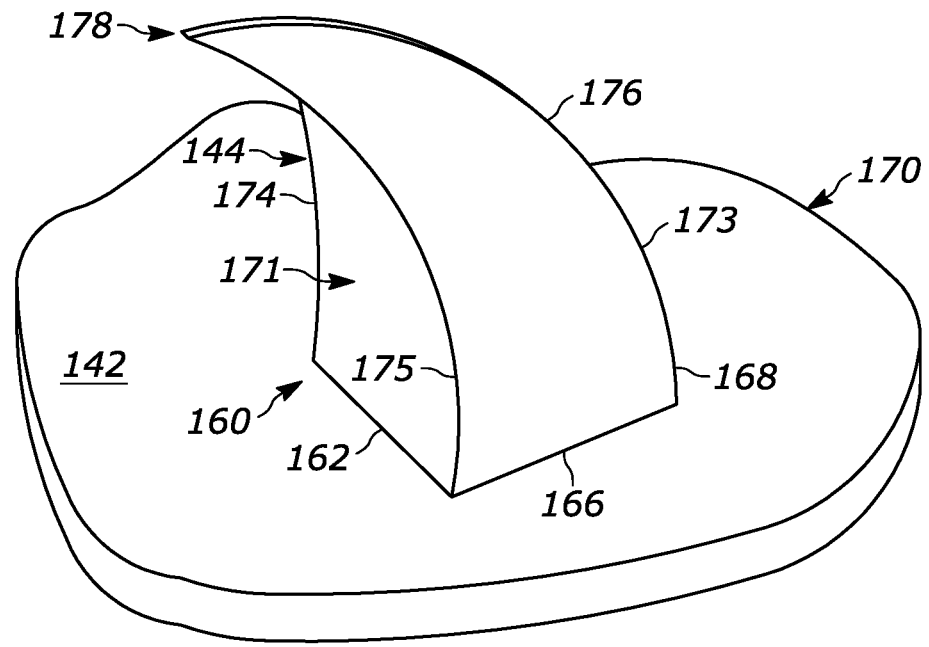
FIG. 12 of the drawings is a perspective view of the gripping structure showing, in particular, an upstanding structure.
Figure 13:
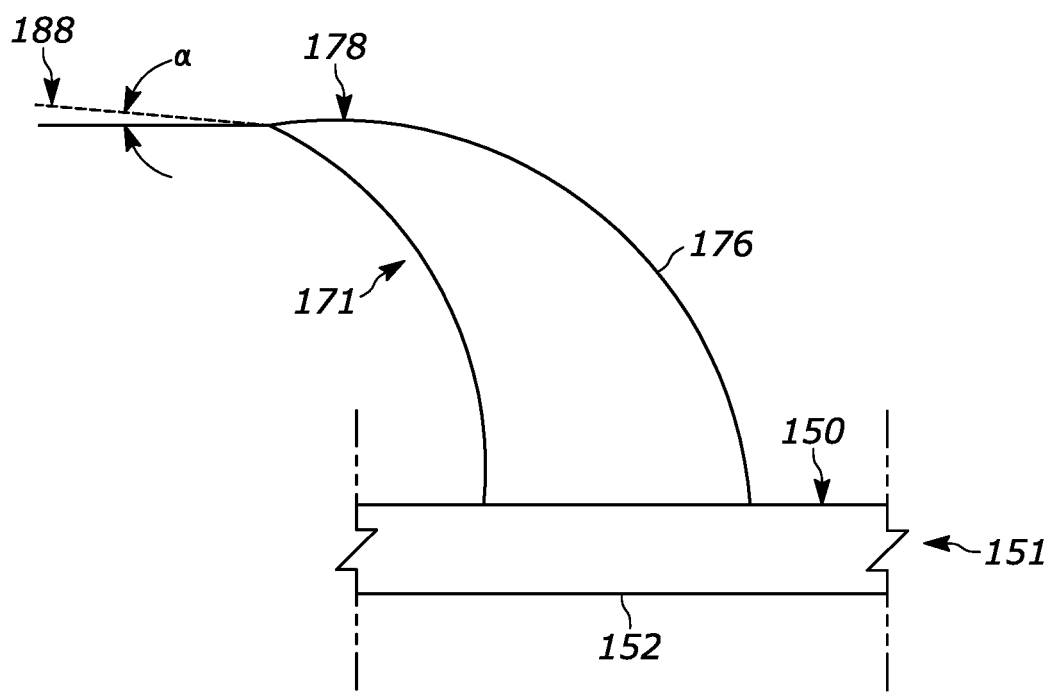
FIG. 13 of the drawings is a cross sectional view of the gripping structure taken generally about lines 13-13 of FIG. 8, showing, in particular, an upstanding structure and the tip.
Figure 14:
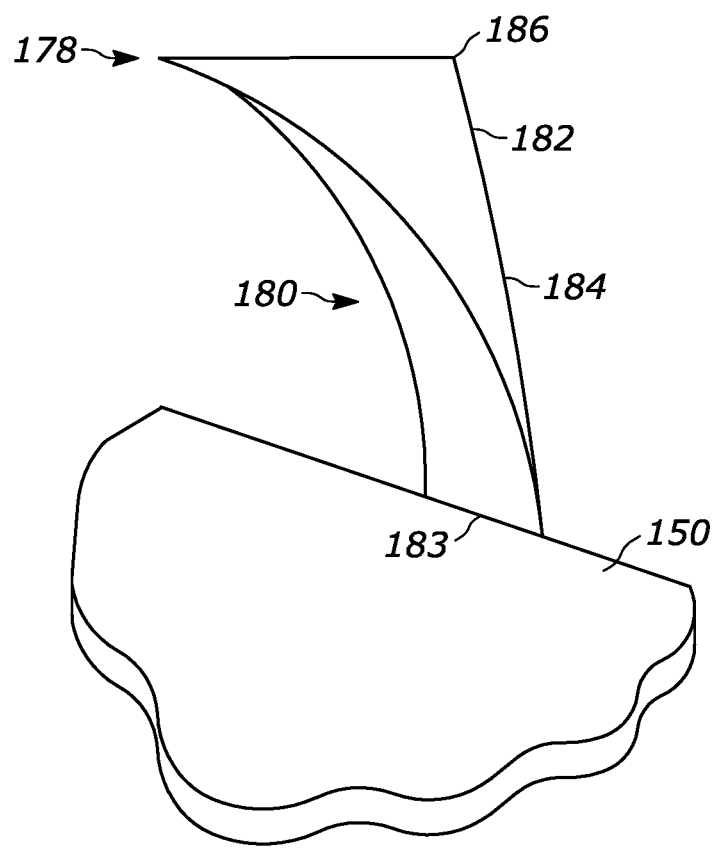
FIG. 14 of the drawings is a perspective cross sectional view of the gripping structure taken generally about lines 14-14 of FIG. 8, showing, in particular, the overhanging portion.
Figure 15:
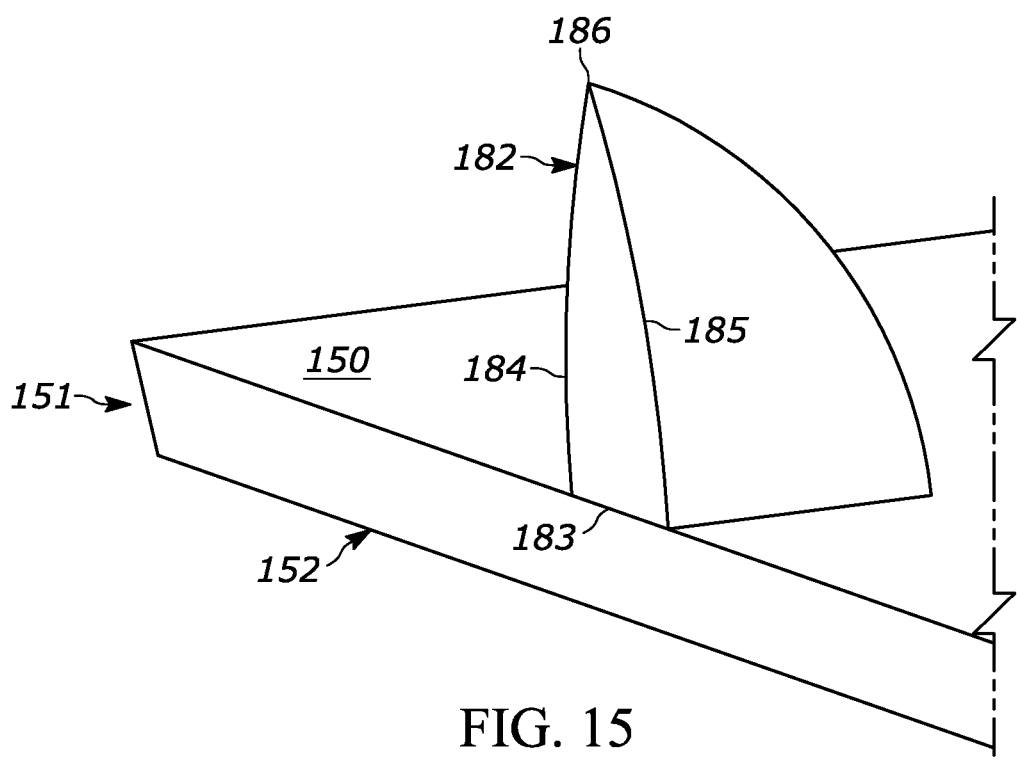
FIG. 15 of the drawings is a perspective cross sectional view of the gripping structure taken generally about lines 15-15 of FIG. 8, showing, in particular, the overhanging portion.

In the deployed configuration, in the configuration shown in FIG. 5b (and also in FIG. 2), the closure apparatus is substantially planar, with the micro needles 29 facing the inner surface of the tissue surrounding the wound opening 102. With reference to FIGS. 6a and 6b, after deployment, the applicator fork can be withdrawn from within the outer sheath, leaving behind the closure apparatus with the string members extending through the outer sheath. The practitioner can then pull on the string members, while retaining the outer sheath in position so that the micro needles 29 engage the inner surface 106 of the tissue. Continued pulling of the string members, embeds the micro needles 29 into the tissue.

At the same time, or closely following, the continued pulling of the string members tends to collapse (or fold) the closure apparatus around the wound opening 102. In the configuration shown, the closure apparatus begins to pull together the tissue around the wound opening. Eventually, and with reference to FIGS. 7a and 7b, the pulling of the string members directs the closure apparatus into the clinching configuration, wherein the closure member has clinched around the wound opening and effectively closed the wound opening.

To maintain the configuration, it is contemplated that in certain configurations, the string members are tied or otherwise manipulated to maintain the clinching configuration. In some procedures, it may be desirable to use additional suture around the wound to maintain the closed configuration. It will be understood that in some configurations it is not necessary to apply any additional suture to the wound. It is contemplated that in some configurations, the closure apparatus may include locking structures which, when a level of clinching is reached, the closure apparatus retains the clinching configuration. In such a configuration, the applicator forks preclude the closure apparatus from reaching the clinching configuration during insertion.

The foregoing description merely explains and illustrates the disclosure and the disclosure is not limited thereto except insofar as the appended claims are so limited, as those skilled in the art who have the disclosure before them will be able to make modifications without departing from the scope of the disclosure.

What is claimed is:

1. A closure apparatus for use in a subcutaneous wound closure assembly comprising:
    a substrate having an inner surface and an outer surface, a central axis and an outer perimeter, the substrate having a plurality of ribs extending radially outward from the central axis toward the outer perimeter, each of the plurality of radial ribs having a plurality of micro needles extending therefrom, the micro needles being spaced substantially equidistantly and axially along each of the radial ribs and extending upwardly from the inner surface of the substrate, the micro needles further having an upstanding structure terminating in a tip, with each of tips directed both upwardly and toward the central axis, and structurally configured to engage the tissue, and, to embed therein sufficient to be able to move tissue; and a plurality of string members, each string member having a grasping end and a closure end, wherein the closure ends are attached to and spaced axially along each of the radial ribs.

2. The closure apparatus of claim 1 wherein the substrate comprises a flexible material.

3. A subcutaneous wound closure assembly comprising:
    a closure apparatus, comprising, a substrate having an inner surface and an outer surface, a central axis and an outer perimeter, the substrate having a plurality of ribs extending radially outward from the central axis toward the outer perimeter, each of the plurality of radial ribs having a plurality of micro needles extending therefrom, the micro needles being spaced substantially equidistantly and axially along each of the radial ribs and extending upwardly from the inner surface of the substrate, the micro needles further having an upstanding structure terminating in a tip, with each of tips directed both upwardly and toward the central axis, and structurally configured to engage the tissue, and, to embed therein sufficient to be able to move tissue an insertion apparatus having an outer sheath and an applicator; and a retracting structure coupled to the closure apparatus;

wherein the insertion apparatus is attachable to the substrate of the closure apparatus, to insert the closure apparatus into a patient, and the retracting structure is structurally configured to manipulate the closure apparatus into a clinching configuration, with the micro needles engaging tissue and being embedded therein.

4. The assembly of claim 3 wherein the retracting structure comprises a plurality of string members.

5. The subcutaneous wound closure assembly of claim 3 wherein the applicator is slidably insertable within the outer sheath.

6. The subcutaneous wound closure assembly of claim 3 wherein the retracting structure comprises a plurality of string members coupled to the closure apparatus and extending through the outer sheath.

7. A method of using a subcutaneous comprising the steps of:

positioning an outer sheath proximate a wound opening with a distal end opening being positioned proximate thereto;

folding a closure apparatus into a folded configuration, the closure apparatus comprising:

a substrate having an inner surface and an outer surface, a central axis and an outer perimeter, the substrate having a plurality of ribs extending radially outward from the central axis toward the outer perimeter, each of the plurality of radial ribs having a plurality of micro needles extending therefrom, the micro needles being spaced substantially equidistantly and axially along each of the radial ribs and extending upwardly from the inner surface of the substrate, the micro needles further having an upstanding structure terminating in a tip, with each of tips directed both upwardly and toward the central axis, and structurally configured to engage the tissue, and, to embed therein sufficient to be able to move tissue;

directing the closure apparatus through the outer sheath beyond the wound opening with an applicator;

unfolding the closure apparatus beyond the wound opening;

engaging tissue surrounding the wound opening with the micro needles;

pulling the closure apparatus with a retracting structure;

directing the closure structure into a clinching configuration with the retracting structure, thereby engaging the micro needles with tissue, and embedding the micro needles in tissue, to, in turn, close the wound opening.

8. The method of claim 7 wherein the wound opening is closed without the need for a suture applied about the wound opening.

* * * * *